(12) United States Patent
Diaz et al.

(10) Patent No.: US 10,311,659 B2
(45) Date of Patent: Jun. 4, 2019

(54) METHOD OF ANALYZING VARIATIONS OF AT LEAST ONE INDICATOR OF THE BEHAVIOR OF A MECHANISM FITTED TO AN AIRCRAFT

(71) Applicant: AIRBUS HELICOPTERS, Marignane (FR)

(72) Inventors: Alexandre Diaz, Saint-Chamas (FR); Kishan Mithalal, Pertuis (FR); Pierre Dousse, Marseilles (FR); Abdelhafid Boutaleb, Vitrolles (FR); Romaric Simonet, Vitrolles (FR); Didier Rochefort, Marseilles (FR)

(73) Assignee: AIRBUS HELICOPTERS, Marignane (FR)

( * ) Notice: Subject to any disclaimer, the term of this patent is extended or adjusted under 35 U.S.C. 154(b) by 0 days.

(21) Appl. No.: 15/833,084

(22) Filed: Dec. 6, 2017

(65) Prior Publication Data

US 2018/0174383 A1 Jun. 21, 2018

(30) Foreign Application Priority Data

Dec. 14, 2016 (FR) ...................................... 16 01771

(51) Int. Cl.
*G07C 5/08* (2006.01)
*G01N 29/04* (2006.01)
(Continued)

(52) U.S. Cl.
CPC .............. *G07C 5/0841* (2013.01); *B64F 5/60* (2017.01); *G01M 13/028* (2013.01);
(Continued)

(58) Field of Classification Search
USPC ........................................................ 701/33.4
See application file for complete search history.

(56) References Cited

U.S. PATENT DOCUMENTS

| 5,974,349 | A | 10/1999 | Levine | |
|---|---|---|---|---|
| 7,802,204 | B2 * | 9/2010 | Merry | ................... G06Q 10/10 715/764 |

(Continued)

FOREIGN PATENT DOCUMENTS

| EP | 0407179 A1 | 1/1991 |
|---|---|---|
| FR | 2900746 A1 | 11/2007 |

OTHER PUBLICATIONS

French Search Report for French Application No. FR 1601771, Completed by the French Patent Office, dated Aug. 16, 2017, 8 pages.

*Primary Examiner* — Tyler D Paige
(74) *Attorney, Agent, or Firm* — Brooks Kushman P.C.

(57) ABSTRACT

A method of analyzing variations of an indicator of the behavior of a mechanism fitted to an aircraft, the indicator being determined from measurements of a physical operating parameter of the mechanism during a mission of the aircraft. The Method includes a storage step of storing the measurements of the physical operating parameter in a storage unit; a first transmission step of transmitting the measurements of the physical operating parameter contained in the storage unit to a communication station; a second transmission step of transmitting the measurements of the physical operating parameter from the communication station to an analysis center; an indicator generation step of generating the indicator performed on the basis of the measurements of the physical operating parameter; and an analysis step of analyzing variations of the indicator.

16 Claims, 1 Drawing Sheet

(51) Int. Cl.
  *B64F 5/60* (2017.01)
  *G01M 13/028* (2019.01)
  *G05B 23/02* (2006.01)
  *G06Q 10/00* (2012.01)
  *G01N 29/44* (2006.01)
  *G07C 5/00* (2006.01)
  *B64D 45/00* (2006.01)
  *B64D 35/00* (2006.01)

(52) U.S. Cl.
  CPC ......... *G01N 29/04* (2013.01); *G01N 29/4445* (2013.01); *G05B 23/0221* (2013.01); *G05B 23/0283* (2013.01); *G06Q 10/20* (2013.01); *G07C 5/008* (2013.01); *G07C 5/0808* (2013.01); *B64D 35/00* (2013.01); *B64D 2045/0085* (2013.01)

(56) References Cited

U.S. PATENT DOCUMENTS

| | | | | |
|---|---|---|---|---|
| 7,984,146 | B2 * | 7/2011 | Rozak | G06Q 10/06 701/29.3 |
| 9,008,892 | B2 * | 4/2015 | Bollapragada | B64F 5/40 701/29.1 |
| 9,550,583 | B2 * | 1/2017 | Szeto | G07C 5/008 |
| 9,811,950 | B2 * | 11/2017 | Nutaro | G07C 5/0808 |
| 2007/0118301 | A1 * | 5/2007 | Andarawis | G01M 5/00 702/33 |
| 2007/0156496 | A1 | 7/2007 | Avery et al. | |
| 2011/0302175 | A1 | 12/2011 | Staaf | |
| 2015/0051786 | A1 * | 2/2015 | Wang | B64F 5/60 701/29.4 |

* cited by examiner

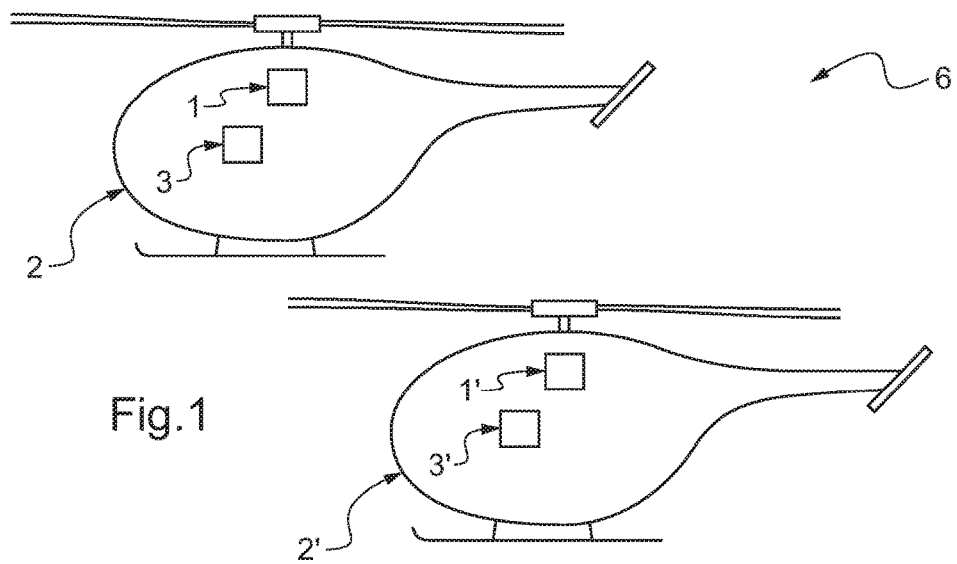
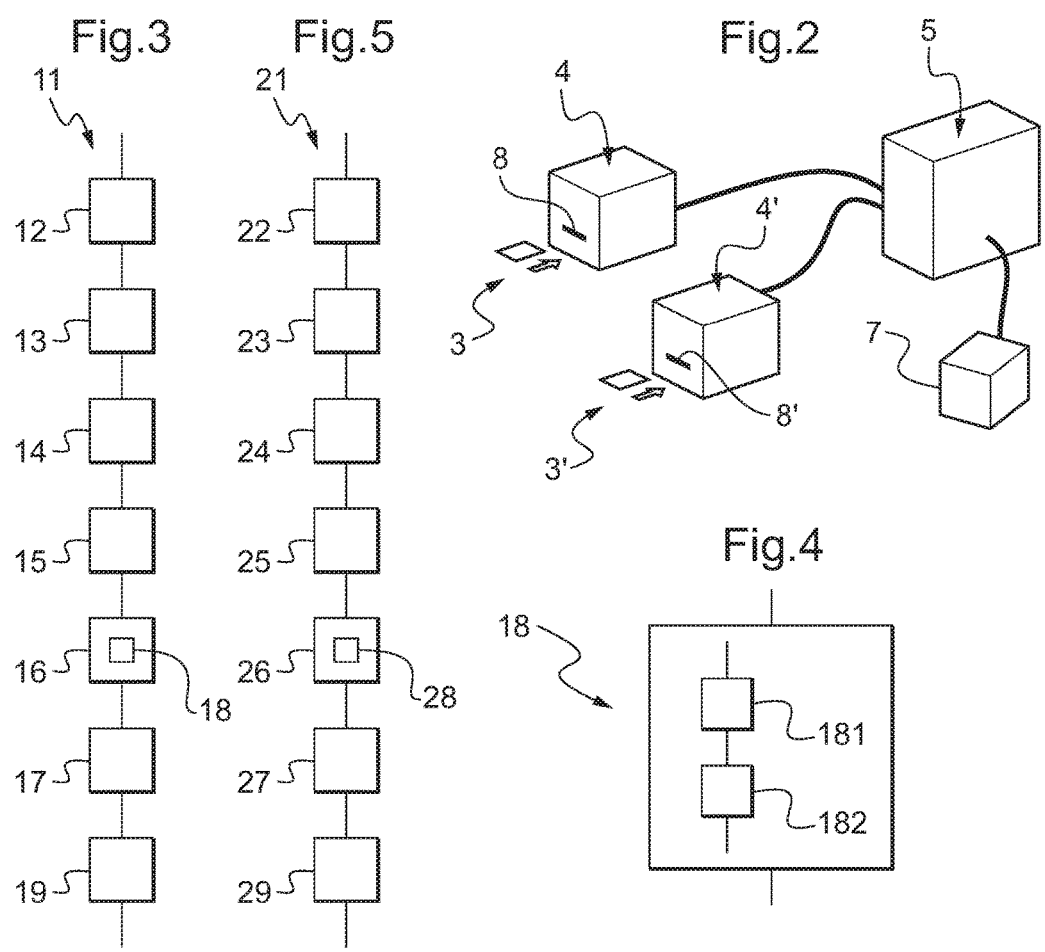

US 10,311,659 B2

METHOD OF ANALYZING VARIATIONS OF AT LEAST ONE INDICATOR OF THE BEHAVIOR OF A MECHANISM FITTED TO AN AIRCRAFT

CROSS-REFERENCE TO RELATED APPLICATIONS

This application claims priority to French patent application No. FR 1601771 filed on Dec. 14, 2016, the disclosure of which is incorporated in its entirety by reference herein.

BACKGROUND OF THE INVENTION

(1) Field of the Invention

The present invention relates to a method of studying the behavior of mechanisms of aircraft, and possibly detecting an anomaly in that behavior in order to be able to anticipate a risk of failure. Such mechanisms are usually movable in rotation. They then comprise power transmission shafts and power transmission means such as gearboxes for transmitting rotary motion, e.g. between one or more engines and a rotor enabling the aircraft to be provided at least with lift and possibly also with propulsion.

More precisely, the invention relates to analyzing variations over time of indicators that are determined from vibration measurements taken in the proximity of one or more mechanisms, these vibration measurements being taken in flight while the aircraft is on a mission. Such indicators are then obtained a posteriori by analyzing the measurements of vibration over time.

(2) Description of Related Art

In order to take such measurements, the aircraft is fitted with accelerometers that are placed (fastened) on the engine(s), on the casing(s) of the gearbox(es), on shaft bearings, and/or on other points of the structure of the aircraft. During a flight, the signals delivered by these sensors are converted into data, and where appropriate synchronized (by signals delivered by a rotation sensor, for example) and/or averaged, and then stored on board the aircraft. On returning to the ground, the stored data is transmitted to a station referred to as a "communication" station serving in particular to read the stored data, and to analyze it or indeed transmit it, e.g. to the manufacturer of the aircraft.

In general manner, and as described in Document FR 2 900 746, interpreting this data is complex and may require a lengthy intervention by an expert.

Known tools for automatically analyzing such data in order to diagnose a mechanical defect in the transmission mechanism are incomplete and imperfect. Specifically, the operator of the aircraft may be alerted in untimely manner, or even too late, about a problem on one of the mechanisms of an aircraft.

Furthermore, that type of analysis method relies on the principle of crossing a limit threshold beyond which an alarm is triggered, which then causes the aircraft to be grounded until a corrective maintenance operation has been performed in order to verify and/or correct the detected problem.

As described in Document EP 0 407 179, a method is also known whereby data measured in flight by sensors on board an aircraft is transmitted to the ground. The data is then analyzed and an alert can be generated if the measured values cross a predetermined threshold.

Thus, as in Document FR 2 900 746, when an alert is triggered, the aircraft is grounded until a corrective maintenance operation is performed to verify and/or correct the detected problem corresponding to the predetermined threshold being crossed.

Furthermore, Document US 2007/156496 A1 describes a method of managing the maintenance of a fleet of aircraft, and more particularly of airplanes. That document thus describes a method in which data coming from a plurality of aircraft of the same type and belonging to at least two operators is transmitted to the manufacturer of the fleet of aircraft.

Nevertheless, under such circumstances, the data is not analyzed to identify a potential problem in the behavior of a mechanism fitted to at least one of the airplanes of the fleet. Consequently, no alerting step is implemented by that method in order to alert the various operators of aircraft fleet about a potential problem on any of their equipment.

In addition, Document U.S. Pat. No. 5,974,349 describes another method of managing corrective maintenance of an aircraft. It serves in particular to alert an operator of the aircraft that a maintenance operation has not been performed in compliance with the flight hours accumulated by a critical part of the aircraft. As before, that method then makes it possible to perform an alerting step only if a flight time limit threshold is crossed by the part in question.

BRIEF SUMMARY OF THE INVENTION

An object of the present invention is thus to propose a method making it possible to avoid the above-mentioned limitations. The object of the invention is to provide a method of analyzing such data that enables the manufacturer of the aircraft to establish a reliable diagnosis on the behavior of a mechanism operating in the aircraft. The aircraft manufacturer can then contact the operator of the aircraft before a threshold is crossed, where such threshold crossing would normally be detected by the communication station installed on the premises of the operator for the purpose of analyzing this data automatically.

The aircraft manufacturer can then anticipate an alarm signal that would be generated by crossing a threshold, and by way of example can make use of a period in which the aircraft is not needed for use in order to perform preventative maintenance operations on the aircraft. In this way, advantage can be taken of periods in which the aircraft is not in use in order to perform the operations of verifying and/or replacing the mechanisms in question in the background. These maintenance operations thus have no consequences on the commercial operations of the aircraft by the operator.

The invention provides a method of analyzing variations of at least one indicator of the behavior of a mechanism fitted to an aircraft, the indicator(s) being determined from measurements of at least one physical operating parameter of the mechanism during a mission of the aircraft, the method comprising at least:

a storage step of storing the measurements of the physical operating parameter(s) in a storage unit;

a first transmission step of transmitting the measurements of the physical operating parameter(s) contained in the storage unit to a communication station external to the aircraft, the communication station being installed on the premises of an operator of the aircraft;

a second transmission step of transmitting the measurements of the physical operating parameter(s) from the communication station to an analysis center external to the aircraft, the analysis center being common to a fleet of aircraft of the same type and being installed on the premises of a manufacturer of the fleet of aircraft;

an indicator generation step of generating the indicator(s) performed on the basis of the measurements of the physical operating parameter (s); and an analysis step of analyzing variations of the indicator(s).

Such a method is remarkable in that the analysis step of analyzing the variations of the indicator(s) is performed on the basis of the measurements of the physical operating parameter(s) of at least two distinct mechanisms fitted to at least two aircraft of the same type belonging to at least two distinct operators, the analysis center serving to analyze the variations of the indicator(s) coming from a first aircraft belonging to a first operator and the variations of the indicator(s) coming from a second aircraft belonging to a second operator, the first and second aircraft being two aircraft of the same type belonging to the fleet of aircraft of the same type, and wherein the method includes a detection step of detecting a potential problem in the behavior of the mechanism fitted to at least one of the aircraft of the fleet and an alerting step enabling the manufacturer of the fleet of aircraft to be alerted to a potential problem in the behavior of the mechanism fitted to at least one of the aircraft of the fleet.

In other words, an analysis center is common to the entire fleet of aircraft of the same type used by different operators. The analysis center then makes it possible for the manufacturer of the fleet of aircraft to analyze simultaneously and/or in succession the indicator(s) coming from the first operator and from the second operator.

The operators can then be contacted by the manufacturer of the fleet of aircraft when the alerting step is performed by the method in accordance with the invention. Such an alerting step is then performed before the indicator(s) crosses a predetermined threshold that would have the consequence of triggering an alarm signal for the operator.

Advantageously, the analysis step of analyzing the variations of the indicator(s) may include a shape analysis substep consisting in comparing the shape of a curve representative of the variations of the indicator(s) with at least one shape of a curve previously stored in a database, the previously stored curve corresponding to a potential problem in the behavior of the mechanism.

In other words, the shape analysis substep makes it possible to identify partial or complete similarity between the curve representative of variations of the indicator(s) and the curve previously stored in the database. Such a database thus makes it possible to list and store a plurality of curves corresponding to a potential problem identified in the behavior of a mechanism. Consequently, such a database varies progressively and can be implemented by the manufacturer each time a potential problem is identified.

In practice, the shape analysis substep may include a subdivision step consisting in subdividing the variations of the indicator(s) into a plurality of samples having the same time dimension corresponding to a reference time dimension representative of the abscissa axis of the previously stored curve.

Thus, the shape analysis substep may begin with a subdivision step serving to take as its reference the time dimension of the abscissa values of the previously stored curve on the basis of a time reference, while acquiring variations in the indicator(s). Such a step then makes it possible to generate a plurality of groups of acquisitions having the same time dimension corresponding to the reference time dimension.

According to an advantageous characteristic of the invention, the shape analysis substep may include a comparison step consisting in using the "least squares" method to compare each of the samples with the previously stored curve.

In this way, the comparison step makes it possible to analyze in reliable and reproducible manner the difference between the previously stored curve and the cloud of points measured while acquiring the variations in the indicator(s).

Also advantageously, the comparison step may serve to determine a percentage compatibility weight for each sample relative to the previously stored curve.

Under such circumstances, the compatibility weight corresponds to the linear correlation coefficient or indeed to a mean of measurements of the dispersion of the cloud of points relative to the previously stored curve.

In an advantageous implementation, the detection step of detecting a potential problem in the behavior of the mechanism fitted to at least one of the aircraft of the fleet may consist in detecting that the compatibility weight exceeds a predefined threshold value.

Consequently, when the compatibility weight is small, no alerting step is implemented by the method in accordance with the invention. Nevertheless, when the compatibility weight reaches the predefined threshold value, which may in a particular implementation be equal to 80%, the alerting step is then implemented by such a method.

In practice, the analysis step of analyzing the variations of the indicator(s) may include a discontinuity analysis substep consisting in identifying a discontinuity in the slope of a tangent to a curve representative of the variations of the indicator(s).

Under such circumstances, the analysis method makes it possible to identify a large change of slope for the tangent to the curve representative of the variations in the indicator(s), which may for example be a point of inflection. Such a substep is also suitable for filtering potential noise in the cloud of points corresponding to acquiring the variations in the indicator(s). In addition, the various curves representative of the variations in the indicator(s) are established by performing linear regression from a cloud of points corresponding to the various measurements. Each linear regression may than be defined by a correlation coefficient representative of the slope of the tangent to the curve.

The analysis method then makes it possible to identify slope discontinuities in the tangents to the various curves representative of the variations in the indicator(s) presenting a correlation coefficient having the same sign, the tangents then being formed solely either by increasing affine functions, or else by decreasing affine functions.

Depending on the capacity for analysis by the manufacturer and on experience corresponding to the problems that have been identified in the behavior of the mechanism by the manufacturer, such an analysis method makes it possible to identify rapid variation in the gradient of the tangent to a curve representative of the variations in the indicator(s).

BRIEF DESCRIPTION OF THE DRAWINGS

The invention and its advantages appear in greater detail from the context of the following description of examples given by way of illustration and with reference to the accompanying figures, in which:

FIG. 1 is a diagram representing a fleet of aircraft enabling the analysis method of the invention to be implemented;

FIG. 2 is a perspective view showing two operator stations connected to an analysis center for performing the method of the invention;

FIG. 3 is a diagram showing a first variant of an analysis method in accordance with the invention;

FIG. 4 is a detail view showing the step of analyzing variations and/or indicator(s) in accordance with the first variant of the analysis method shown in FIG. 3; and FIG. 5 is a diagram showing a second variant of an analysis method in accordance with the invention.

DETAILED DESCRIPTION OF THE INVENTION

As mentioned above, and as shown in FIG. 1, the invention relates to a method of analyzing variations in at least one indicator relating to the behavior of a mechanism 1, 1' fitted to an aircraft 2, 2' of a fleet 6 of aircraft 2, 2' of the same type belonging to at least two distinct operators. Furthermore, the indicator(s) is/are determined on the basis of measuring at least one physical operating parameter of the mechanism 1, 1' during a mission of the aircraft 2, 2'.

Such measurements of at least one physical operating parameter of the mechanism 1, 1' are then obtained by sensors that are sensitive to this at least one physical operating parameter. By way of example, such sensors may thus comprise unidirectional or multidirectional accelerometers. The measurements of the physical operating parameter(s) of the mechanism 1, 1' are then stored in a storage unit 3, 3' during each mission of the aircraft 2, 2'.

Following the end of the mission of the aircraft 2, 2', and as shown in FIG. 2, such a method transfers the measurements of the physical operating parameter(s) of the mechanism 1, 1' as contained in the storage unit 3, 3' to a communication station 4, 4', as installed on the premises of at least two distinct operators.

By way of example, such a storage unit 3, 3' may be in the form of a memory card or indeed of a removable external hard disk. An operator can then disconnect the storage unit 3, 3' from the aircraft 2, 2' when it is on the ground and subsequently insert it in a compatible reader port 8, 8' arranged in the communication station 4, 4'. The reader port 8, 8' thus makes it possible to read and transfer the data contained in the storage unit 3, 3' to the communication station 4, 4'.

Furthermore, these various communication stations 4 and 4' installed on the premises of the different operators of aircraft 2 and 2' are then connected to an analysis center 5, which is installed on the premises of the manufacturer of the fleet of aircraft 2, 2'. This connection preferably makes use of a secure Internet connection and thus enables the analysis center 5 to analyze the physical operating parameter(s) of the mechanism 1, 1' coming from two operators of aircraft 2, 2' that are physically very remote from the analysis center 5.

Furthermore, indicators are then generated by the communication station 4, 4' and/or by the analysis center 5 on the basis of the measurements taken by the sensors sensitive to the physical operating parameter(s) of the mechanism 1, 1'.

Such indicators are then analyzed in accordance with the analysis methods described in FIGS. 3 to 5 that include a step 16, 26 of analyzing variations in the indicator(s).

In a first variant of the invention corresponding to the analysis method 11, such variations may advantageously be compared with curves previously stored in a database 7 containing various curves representative of a potential problem in the operation of the mechanism 1, 1' and previously identified by the manufacturer of the fleet 6 of aircraft 2, 2'.

As shown in FIG. 3, in the first variant of the invention, the method 11 serves to analyze variations in at least one indicator of the behavior of a mechanism 1, 1' fitted to an aircraft 2, 2'. In addition, such a method 11 comprises at least:

a storage step 12 of storing the measurements of the physical operating parameter(s) in a storage unit 3, 3';

a first transmission step 13 of transmitting the measurements of the physical operating parameter(s) contained in the storage unit 3, 3' to the communication station 4, 4' external to the aircraft 2, 2';

a second transmission step 14 of transmitting the measurements of the physical operating parameter(s) from the communication station 4, 4' to the analysis center 5 external to the aircraft 2, 2';

an indicator generation step 15 of generating the indicator(s) derived from the measurements of the physical operating parameter(s);

an analysis step 16 of analyzing variations in the indicator(s);

a detection step 17 of detecting a potential problem in the behavior of the mechanism 1, 1' fitted to at least one of the aircraft 2, 2' of the fleet 6; and an alerting step 19 serving to alert the manufacturer of the fleet 6 of aircraft 2, 2' of a potential problem in the behavior of the mechanism 1, 1' fitted to at least one of the aircraft 2, 2'.

Furthermore, such a step 16 of analyzing the variations of the indicator(s) is performed on the basis of said measurements of the physical operating parameter(s) of at least two mutually distinct mechanisms 1 and 1' that are fitted to at least two aircraft 2 and 2' of the same type belonging to at least two distinct operators. Under such circumstances, the analysis center 5 is then configured to analyze the variations of the indicator(s) coming from a first aircraft 2 belonging to a first operator and the variations of the indicator(s) coming from a second aircraft 2' belonging to a second operator.

As mentioned above, the first and second aircraft 2 and 2' are then two aircraft of the same type belonging to the fleet 6 of aircraft 2, 2' of the same type. The different variations of the indicator(s) coming from the first and second aircraft 2 and 2' can then be analyzed either simultaneously or successively, depending on the computation capacity of the analysis center 5.

Furthermore, in this first variant of the invention, as shown in FIG. 3, the step 16 of analyzing the variations in the indicator(s) comprises a shape analysis substep 18 consisting in comparing the shape of a curve representative of variations in the indicator(s) with at least one shape of a curve previously stored in the database 7.

As shown in FIG. 4, this shape analysis substep 18 may itself comprise a subdivision step 181 consisting in subdividing the variations in the indicator(s) into a plurality of samples having the same time dimension corresponding to a reference time dimension representative of the curve previously stored in the database 7.

In addition, the shape analysis substep 18 may also include a comparison step 182 consisting in using the "least squares" method to compare each of the samples with the curve previously stored in the database 7.

In a second variant of the analysis method 21 in accordance with the invention, and as shown in FIG. 5, the method 21 comprises at least:

a storage step 22 of storing the measurements of the physical operating parameter(s) in a storage unit 3, 3';

a first transmission step 23 of transmitting the measurements of the physical operating parameter(s) contained in the storage unit 3, 3' to the communication station 4, 4' external to the aircraft 2, 2';

a second transmission step 24 of transmitting the measurements of the physical operating parameter(s) from the communication station 4, 4' to the analysis center 5 external to the aircraft 2, 2';

an indicator generation step 25 of generating the indicator(s) derived from the measurements of the physical operating parameter(s);

an analysis step 26 of analyzing variations in the indicator(s);

a detection step 27 of detecting a potential problem in the behavior of the mechanism 1, 1' fitted to at least one of the aircraft 2, 2' of the fleet 6; and an alerting step 29 serving to alert the manufacturer of the fleet 6 of aircraft 2, 2' of a potential problem in the behavior of the mechanism 1, 1' fitted to at least one of the aircraft 2, 2'.

In this second variant of the invention, the step 26 of analyzing the variations in the indicator(s) includes a discontinuity analysis substep 28 consisting in identifying a discontinuity in a slope of a tangent to a curve representative of the variations of the indicator(s).

As mentioned above, during this discontinuity analysis substep 28, the various curves representative of the variations in the indicator(s) are established by performing linear regression from a cloud of points corresponding to the various measurements. Each linear regression may then be defined by a correlation coefficient representative of the slope of the tangent to the curve.

Such an analysis method 21 then makes it possible to identify slope discontinuities for tangents to the various curves representative of the variations in the indicator(s) presenting a correlation coefficient having the same sign, the tangents then being formed solely either by increasing affine functions or by decreasing affine functions.

In addition, such a discontinuity analysis substep 28 serves to identify a sudden variation in the gradient of the tangent to the curve representative of the variations in the indicator(s).

Naturally, the present invention may be subjected to numerous variations as to its implementation. Although several implementations are described, it will readily be understood that it is not conceivable to identify exhaustively all possible implementations. It is naturally possible to envisage replacing any of the means described by equivalent means without going beyond the ambit of the present invention.

What is claimed is:

1. A method of analyzing variations of at least one indicator of the behavior of a mechanism fitted to an aircraft that is a member of a fleet of aircraft of a same type, the at least one indicator being determined from measurements of at least one physical operating parameter of the mechanism during a mission of the aircraft, the method comprising:

a storage step of storing the measurements of the at least one physical operating parameter in a storage unit;

a first transmission step of transmitting the measurements of the at least one physical operating parameter contained in the storage unit to a communication station external to the aircraft, the communication station being installed on the premises of an operator of the aircraft;

a second transmission step of transmitting the measurements of the at least one physical operating parameter from the communication station to an analysis center external to the aircraft, the analysis center being common to the fleet of aircraft of the same type and being installed on the premises of a manufacturer of the fleet of aircraft;

an indicator generation step of generating the at least one indicator performed based on the measurements of the at least one physical operating parameter; and an analysis step of analyzing variations of the at least one indicator;

wherein the analysis step of analyzing the variations of the at least one indicator is performed based on the measurements of the at least one physical operating parameter of at least two distinct mechanisms fitted to at least two aircraft of the same type belonging to at least two distinct operators, the analysis center serving to analyze the variations of the at least one indicator coming from a first aircraft belonging to a first operator and the variations of the at least one indicator coming from a second aircraft belonging to a second operator, the first and second aircraft being two aircraft of the same type belonging to the fleet of aircraft of the same type, and wherein the method includes a detection step of detecting a potential problem in the behavior of the mechanism fitted to at least one of the aircraft of the fleet and an alerting step enabling the manufacturer of the fleet of aircraft to be alerted to a potential problem in the behavior of the mechanism fitted to at least one of the aircraft of the fleet.

2. The method according to claim 1, wherein the analysis step of analyzing the variations of the at least one indicator includes a shape analysis substep consisting in comparing the shape of a curve representative of the variations of the at least one indicator with at least one shape of a curve previously stored in a database, the previously stored curve corresponding to a potential problem in the behavior of the mechanism.

3. The method according to claim 2, wherein the shape analysis substep includes a subdivision step consisting in subdividing the variations of the at least one indicator into a plurality of samples having the same time dimension corresponding to a reference time dimension representative of the abscissa axis of the previously stored curve.

4. The method according to claim 3, wherein the shape analysis substep includes a comparison step consisting in using the "least squares" method to compare each of the samples with the previously stored curve.

5. The method according to claim 4, wherein the comparison step serves to determine a percentage compatibility weight for each sample relative to the previously stored curve.

6. The method according to claim 5, wherein the detection step of detecting a potential problem in the behavior of the mechanism fitted to at least one of the aircraft of the fleet consists in detecting that the compatibility weight exceeds a predefined threshold value.

7. The method according to claim 1, wherein the analysis step of analyzing the variations of the at least one indicator includes a discontinuity analysis substep consisting in identifying a discontinuity in the slope of a tangent to a curve representative of the variations of the at least one indicator.

8. The method according to claim 1, wherein a physical operating parameter of the at least one physical operating parameter is vibration.

9. A method comprising:

conducting measurements of a physical operating parameter of a first mechanism of a first aircraft during a mission of the first aircraft and of a physical operating parameter of a second mechanism of a second aircraft during a mission of the second aircraft, wherein the first aircraft belongs to a first operator, the second aircraft belongs to a second operator, the first aircraft and the second aircraft are of a fleet of aircraft of a same type, and the fleet of aircraft is of a same manufacturer;

storing the measurements of the physical operating parameter of the first mechanism of the first aircraft in a first storage unit on-board the first aircraft and storing the measurements of the physical operating parameter of the second mechanism of the second aircraft in a second storage unit on-board the second aircraft;

transmitting the measurements of the physical operating parameter of the first mechanism of the first aircraft stored in the first storage unit to a first communication station external to the first aircraft and transmitting the measurements of the physical operating parameter of the second mechanism of the second aircraft stored in the second storage unit to a second communication station external to the second aircraft, wherein the first communication station is installed on premises of the first operator and the second communication station is installed on premises of the second operator;

transmitting the measurements of the physical operating parameter of the first mechanism of the first aircraft from the first communication station to an analysis center and transmitting the measurements of the physical operating parameter of the second mechanism of the second aircraft from the second communication station to the analysis center, wherein the analysis center is installed on premises of the manufacturer of the fleet of aircraft;

generating, at the analysis center, a first indicator based on the measurements of the physical operating parameter of the first mechanism of the first aircraft and a second indicator based on the measurements of the physical operating parameter of the second mechanism of the second aircraft;

analyzing, at the analysis center, variations of the indicators; and detecting for a potential problem in behavior of at least one of the mechanisms from the analysis of the variations of the indicators and alerting the manufacturer of the fleet of aircraft upon the potential problem being detected.

10. The method according to claim 9, wherein analyzing variations of the indicators includes comparing shapes of curves representative of the variations of the indicators with a shape of a curve previously stored in a database of the analysis center, the previously stored curve corresponding to a potential problem in the behavior of at least one of the mechanisms.

11. The method according to claim 10, wherein analyzing variations of the indicators further includes subdividing the variations of the indicators into a plurality of samples having the same time dimension corresponding to a reference time dimension representative of the abscissa axis of the previously stored curve.

12. The method according to claim 11, wherein analyzing variations of the indicators further includes using the "least squares" method to compare each of the samples with the previously stored curve.

13. The method according to claim 12, wherein comparing each of the samples with the previously stored curve serves to determine a percentage compatibility weight for each sample relative to the previously stored curve.

14. The method according to claim 13, wherein detecting for a potential problem in behavior of at least one of the mechanisms includes detecting whether the percentage compatibility weight for each sample exceeds a predefined threshold value.

15. The method according to claim 9, wherein analyzing variations of the indicators includes identifying a discontinuity in the slope of a tangent to curves representative of the variations of the indicators.

16. The method according to claim 9, wherein the physical operating parameter of the mechanism of each of the first and second aircrafts is vibration.

* * * * *